United States Patent [19]
Leibersperger et al.

[11] Patent Number: 5,951,570
[45] Date of Patent: Sep. 14, 1999

[54] INTRACORPORAL TREATMENT SYSTEM

[75] Inventors: Wolfgang Leibersperger, Tuttlingen; Klaus Irion, Liptingen, both of Germany

[73] Assignee: Karl Storz GmbH & Co., Germany

[21] Appl. No.: 08/930,530

[22] PCT Filed: Apr. 24, 1996

[86] PCT No.: PCT/DE96/00720

§ 371 Date: Oct. 17, 1997

§ 102(e) Date: Oct. 17, 1997

[87] PCT Pub. No.: WO96/33661

PCT Pub. Date: Oct. 31, 1996

[30] Foreign Application Priority Data

Apr. 24, 1995 [DE] Germany .......................... 195 14 440
Sep. 26, 1995 [DE] Germany .......................... 195 35 828

[51] Int. Cl.[6] ................................................. A61B 17/22
[52] U.S. Cl. ........................................................... 606/128
[58] Field of Search .................................. 606/128, 127, 606/107, 167, 19, 22, 902, 170, 171, 184, 185

[56] References Cited

U.S. PATENT DOCUMENTS 3,792,701  2/1974  Kloz et al. ................................. 128/7
3,913,585  10/1975  Wolvek ..................................... 128/305
5,160,336  11/1992  Favre ........................................ 606/128

Primary Examiner—Michael Buiz
Assistant Examiner—Vy Q. Bui
Attorney, Agent, or Firm—St.Onge Steward Johnston & Reens LLC

[57] ABSTRACT

Disclosed is an intracorporal treatment system for crushing concretions, such as stones in the urinary tract, calcium deposits in the blood vessels or bone cement, having

- a thrust unit which accelerates a thrust element in an acceleration path in such a manner that it impinges upon a target, and
- a thrust transmitter designed as a probe which can be inserted into a human body and which is moved by the target in order to transmit the thrust to the treatment site.

The invented treatment system is distinguised by the fact that the axes of the acceleration path and the thrust transmitter are offset and that said target is a non-axially acting transformation element which transmits the kinetic energy of said thrust element onto the proximal end of said thrust transmitter.

17 Claims, 3 Drawing Sheets

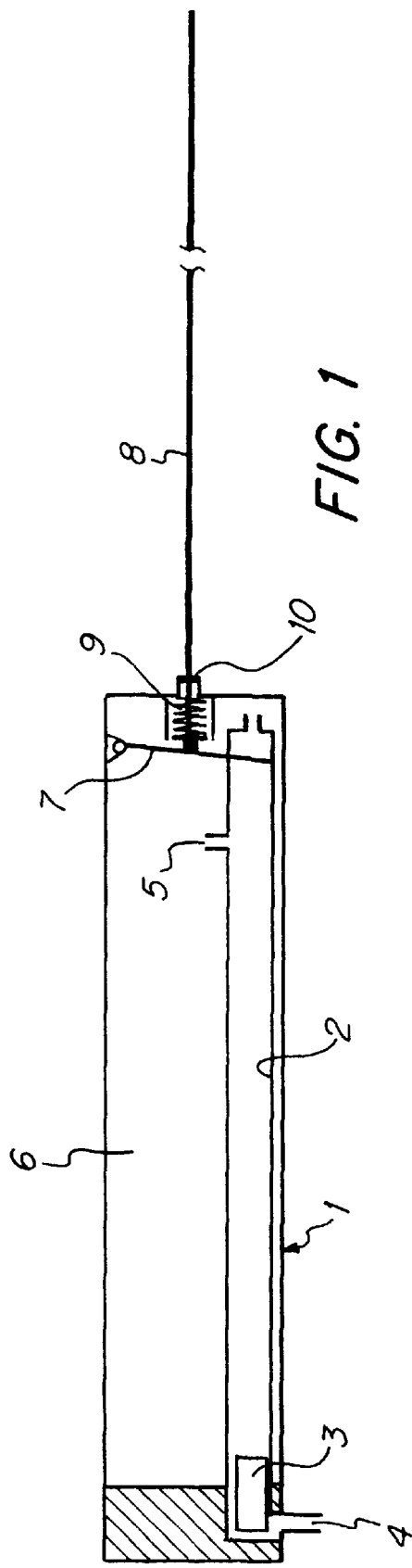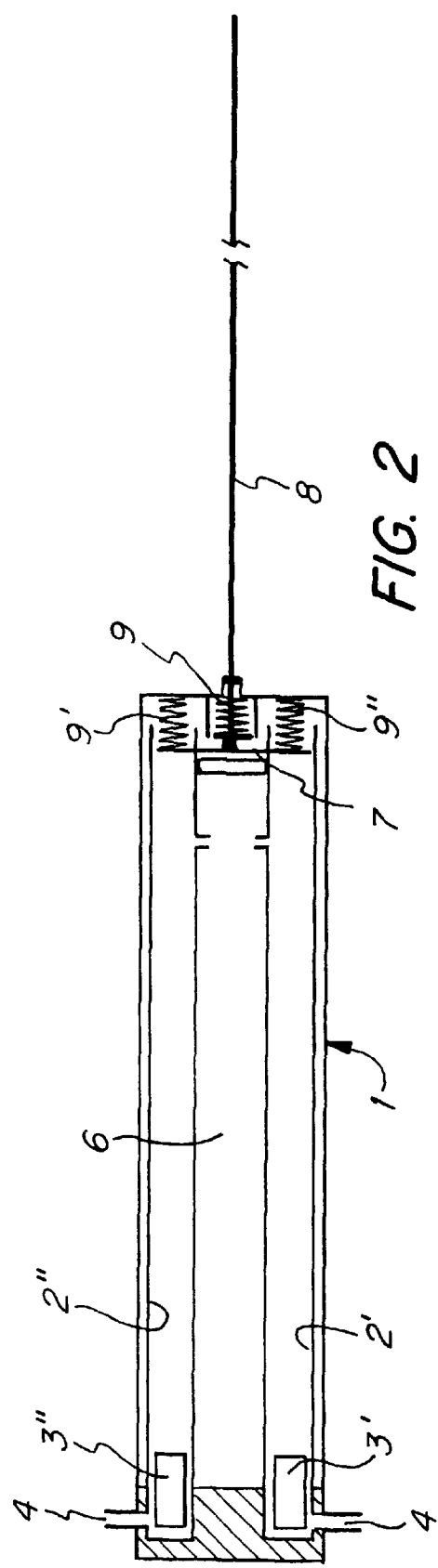

INTRACORPORAL TREATMENT SYSTEM

TECHNICAL FIELD

The present invention relates to an intracorporal treatment system for crushing concretions, such as stones in the urinary tract, calcium deposits in the blood vessels or bone cement according to the generic part of claims 1 respectively 2.

STATE OF THE ART

An intracorporal treatment system of this type is known from U.S. Pat. No. 5,160,336 respectively EP 0317 507 B1 with for the most part the same content.

Largely the same treatment systems are known from DE 38 26 414 A1, DE 43 13 768 A1, OE printed patent 309 663 or OE printed patent 321 448.

The intracorporal treatment systems known from U.S. Pat. No. 5,160,336 or EP 0 317 507 have a thrust unit which accelerates a projectile in an acceleration path in such a manner that it impinges on a target. The acceleration path is in this case a tube in which the projectile can be moved to and fro. Through an air inlet provided at the opposite end of the tube from the target, the projectile can be accelerated by compressed air or the like in such a manner that it impinges on the target with great kinetic energy.

The target, which is in the prior art system a "thrust transmitting window" at the distal end of the acceleration path, transmits the kinetic energy of the projectile to the thrust transmitter which by this means is abruptly moved, i.e. in a thrust-shaped or elongated manner. The thrust transmitter can, by way of illustration, be a high-performance metal wire. By excursion of the thrust transmitter, the to-be-crushed concretion, by way of illustration a urinary stone or the like, is destroyed.

Provided in the treatment system known from DE 38 26 414 A1 is an ultrasonic vibrator which generates the energy by means of which the thrust transmitter is impinged.

DE 43 13 768 A1 describes a treatment system in which a soft iron mass body is accelerated by a magnetic field generated by a coil. The mass body transmits its kinetic energy upon impact with the thrust transmitter thereupon.

Finally treatment systems are known from the aforementioned OE printed patents in which light energy respectively the energy of a spark gap transmitted via a membrane to the thrust transmitter serves to excite the thrust transmitter.

All the prior art intracorporal treatment systems which work with a projectile respectively a mass body have in common that the linear acceleration path for the projectile and the thrust transmitter is aligned strictly axially.

The treatment systems known from OE printed patents employ an axially aligned setup.

Due to the axial alignment of the setup, the prior art treatment systems and, in particular, the prior art generic intracorporal treatment system, as was understood as an element of the present invention, have a number of drawbacks:

1. The magnitude of the excursion, i.e., the elongation of the thrust transmitter can only be adjusted to a certain extent via the impinging pressure.
2. Although the use of a pneumatic system for moving the projectile has the advantage that the projectile can hit the target with relatively high frequency. In a number of instances, by way of illustration, when the concretion to be destroyed is not held in a cage, this high "shooting frequency" is not really needed, because the impact of the thrust transmitter impinging upon the concretion moves the concretion so that the treatment system has to be realigned to the concretion.
   In these case, the prior art intracorporal treatment system is unnecessarily complicated and expensive.
3. The prior art intracorporal treatment system does not permit the integration of a suction channel respectively rinsing channel.

DESCRIPTION OF THE INVENTION

The object of the present invention is to provide an intracorporal treatment system for crushing concretions, such as stones in the urinary tract, calcium deposits in the blood vessels or bone cement, in which at least one of the aforementioned drawbacks of the prior art generic intracorporal treatment systems is eliminated, thus by way of illustration the elongation of the thrust transmitter can be set.

The measures claimed in the independent claims can, of course, be combined.

For setting of the elongation, in an invented embodiment, the longitudinal axes of the acceleration path and the thrust transmitter radially offset, i.e. there is a space in the direction transverse to their generally parallel aligned longitudinal axes. By this means, a non-axially acting transformation element, which in particular can be a lever but also another transmitter and which transmits the kinetic energy of the thrust element, by way of illustration designed as a projectile, to the proximal end of the thrust transmitter, can be placed between the acceleration path and the thrust transmitter. This transformation element also serves as a target for the thrust element.

Relinquishing the collinear arrangement of the acceleration path for the thrust element and the thrust transmitter provided in the state of the art, owing to which the use of a transformer becomes possible, with a specific, by way of illustration determined by the application, kinetic energy of the thrust element, the elongation, i.e. the excursion of the thrust transmitter from its resting position in which it, by way of illustration, just does not happen to be touching a calculus, can be set to a desired value.

In particular if a lever system is employed as the transformer element, the length of the lever can be made adjustable in such a manner that the elongation of the thrust transmitter can be set not only by the manufacturer but also during operation of the invented treatment system.

Moreover, the invented arrangement in which the axes of the acceleration path and of the thrust transmitter are offset permits providing multiple acceleration paths with one thrust element each. All the thrust elements can impinge upon a single transformation element.

The single thrust elements can be triggered in such a manner that they transmit their kinetic energy simultaneously to the thrust transmitter, thereby permitting a substantial rise in the energy coupled into the thrust transmitter.

Furthermore, the kinetic energy of multiple thrust elements can be coupled into the thrust transmitter in short succession in comparison to the pulse duration of the thrusts. The interval between the individual thrusts can be predetermined in such a manner that the individual thrusts overlap so that the site to be treated is impinged upon with high thrust energy in short sequences in a type of "jolting device".

The thrust elements can be designed in a variety of ways:

By way of illustration, projectiles that are moved in an acceleration path can be employed as thrust elements.

Furthermore, for example, cocking levers which move on a sector of a circle and which are designed like the cocking lever of a revolver can be utilized.

The use of axially or extra axially disposed cocking levers has the particular advantage that their buildup is relatively simple so that treatment systems provided with them can be manufactured inexpensively, in particular if a manually tensioned spring is utilized as a drive for each cocking lever.

Naturally, other drive systems can be employed beside springs. By way of illustration, especially if projectiles, like in the state of art, are employed as thrust elements, pneumatic drive systems in which the projectile is impinged upon with compressed air from the proximal side, by way of illustration from a compressed air tank can be utilized.

Of course, other systems can also be employed to drive the projectiles such as, by way of illustration, electromagnetic acceleration systems, piezoelectric systems or ultrasonic systems as described in the printed publications cited in the introduction.

Claims 11 and 12 describe various possible ways of designing the projectiles. In order to reduce the friction, the projectile or projectiles can have a basic cylindrical shape with a rounded front surface and lateral contractual rings or can be designed as balls.

In a further invented embodiment, the thrust invented transmitter is a hollow probe. The channel of the hollow probe can serve as a suction or rinsing channel. Alternatively, the probe of another lithotripsy system, such as of an electrohydraulic system, can be inserted into the channel. Furthermore, an acoustical sensor which permits stone/soft-tissue detection can be provided at the proximal end of the hollow probe.

The embodiment in which the thrust transmitter is a hollow probe can still be employed if an non-axially acting transformation element is employed as well as in an axial arrangement of the thrust unit and the thrust transmitter. In the latter case, the hollow probe runs at its proximal end into a continuing tube on which the thrust element having an axial borehole slides.

BRIEF DESCRIPTION OF THE DRAWING

The present invention is made more apparent in the following using preferred embodiments with reference to the accompanying drawings depicting :

FIG. 1 a first preferred embodiment of the present invention having one acceleration path, FIG. 2 a second preferred embodiment of the present invention having two acceleration paths, FIG. 3 a third preferred embodiment in which a cocking lever is employed as the thrust element, and FIGS. 4a and 4b two alternatives of a fourth preferred embodiment in which the thrust transmitter is a hollow probe.

DESCRIPTION OF PREFERRED EMBODIMENTS

Figure 4A:
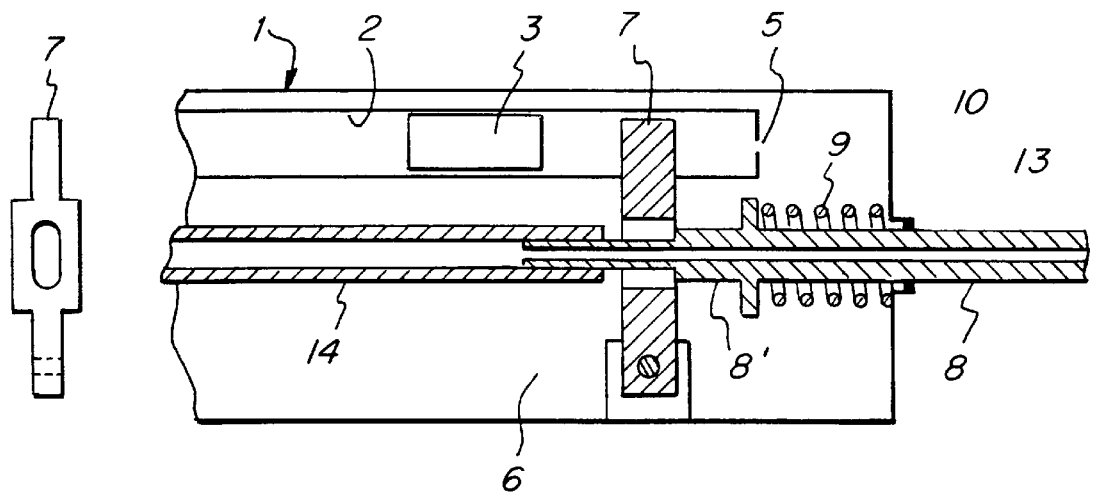

FIG. 1 shows a first preferred embodiment of an invented intracoporal treatment system. Disposed in a housing 1 is a thrust unit which is provided with an acceleration path 2 for a projectile 3.

Acceleration path 2 is composed of a tube which is provided at it is proximal end with an inlet 4 and at its distal end with an outlet 5. The projectile possesses a basic cylindrical shape with a rounded front surface and lateral contractual rings.

Outlet 5 leads into the interior space 6 of housing 1. Inlet 4 is connected, in a similar manner as described in U.S. Pat. No. 5,160,336, to a compressed air source, which can by way of illustration have a compressed air tank, and if need be, to a suction pump. The low pressure supports the "return" of the projectile from the distal end position. Of course, however, another source of compressed air, an electromagnetic, a piezoelectric or a magnetorestrictive drive or a linear drive, can be utilized instead of a compressed air tank.

In the depicted preferred embodiment, suited application of overpressure or low pressure at inlet 4, projectile 3 is accelerated in such a manner that it impinges on a lever 7 which is joined to housing 1 and which, in addition, impinges on a thrust transmitter 8 which is designed as a probe. The thrust transmitter can be inserted into the body and is moved by the target in order to transmit the thrust to the treatment site. Reference number 9 stands for a return spring. 10 stands for a sealing of housing 1. In particular, an "active" return of projectile 3 by means of low pressure permits attaining thrust frequencies between 10 and more than 30 Hz.

FIG. 1 shows that the longitudinal axes of the acceleration path 2 and the thrust transmitter 8 are offset. The transmission of the kinetic energy of projectile 3 to thrust transmitter 8 is achieved by lever 7, which serves as a non-axially acting transmission element. By means of the kinetic energy of the projectile 3, the thrust transmitter 8 is ejected "thrustlike" by an elongation path which is determined by the geometry of lever 7 and the buffing of lever 7 in the tube 2. The elongation can be varied according to the respective application by changing the lever conditions.

Figure 3:
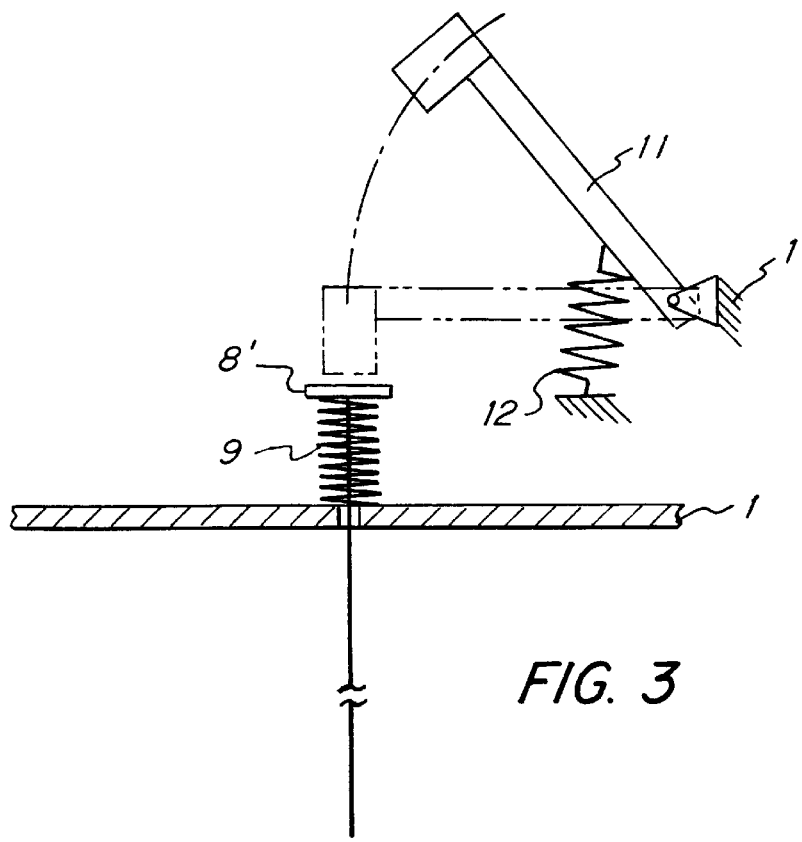

FIGS. 2 to 4 show further embodiments of the present invention in which the same or corresponding parts bear the same reference numbers as in FIG. 1, thus obviating renewed presentation of these parts.

The preferred embodiment depicted in FIG. 2 has two acceleration paths 2' and 2" having a projectile 3' and 3" respectively. Both projectiles 3' and 3" hit a lever system 7' which couples in the kinetic energy of the projectiles into the single thrust transmitter 8.

Triggering of the projectiles can occur in such a manner that the kinetic energy of both projectiles is coupled into the thrust transmitter simultaneously or in short succession in comparison to the pulse width of a thrust.

In the preferred embodiments shown in FIGS. 1 and 2, a pneumatic system drives the projectile or projectiles. Of course, as already explained, other drive systems, such as electromagnetic or piezo systems can also be utilized.

FIG. 3 shows a third preferred embodiment of the present invention in which a thrust unit having a cocking lever 11, which is manually tensioned against the force of a spring 12, is disposed in housing 1. Upon releasing the cocking lever 11, the cocking lever 11 impinges upon the proximal end 8' of the thrust transmitter 8 which is borne in a moveable manner in the housing against the force of spring 9. The impact of the impinging cocking lever 11 (drawn with dotted lines) moves the thrust transmitter 8 and has in this manner a destructive effect on the concretion, etc.

Figure 4B:
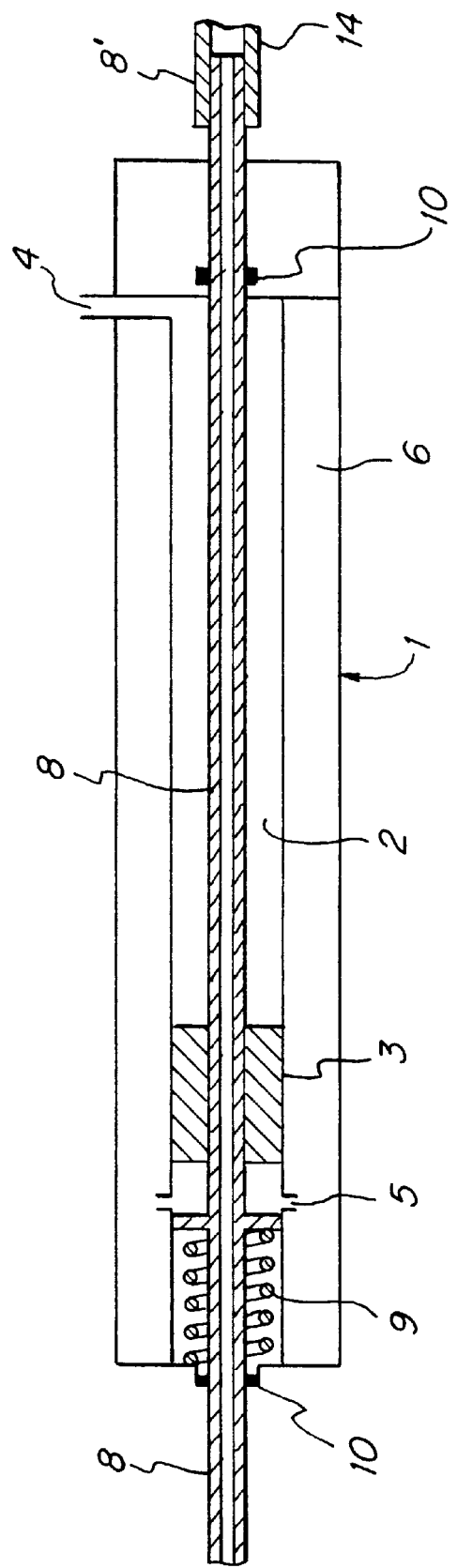

FIGS. 4a and 4b show two alternatives of a fourth preferred embodiment, in which the thrust transmitter 8 is a hollow probe.

In the preferred embodiment shown in FIG. 4a, the axes of the acceleration path 2 and the thrust transmitter 8 are offset. Like in the preferred embodiment depicted in FIG. 1, a lever 7 serving as a non-axially acting transformation element transmits the kinetic energy of the thrust element, designed as projectile 3, to the proximal end 8' of the thrust transmitter 8. The channel 13 provided in thrust transmitter 8 is connected via a tube 14 to a suction or rinsing source.

In the preferred embodiment depicted in FIG. 4b, the acceleration path 2 and the thrust transmitter 8 designed as a hollow probe are disposed coaxially. The hollow probe 8 runs at its proximal end 8' into a continuing pipe 14, which the projectile 3 provided with an axial borehole which slides over said hollow probe.

What is claimed is:

1. An intracorporal treatment system for crushing concretions at a treatment site, such as stones in the urinary tract, calcium deposits in the blood vessels or bone cement, having
    a thrust unit which accelerates a thrust element in an acceleration path in such a manner that it impinges upon a target, and
    a trust transmitter designed as a probe which can be inserted into a human body and which is moved by the target in order to transmit the thrust to the treatment site, characterized by the fact that axes of the acceleration path and the thrust transmitter are radially offset and that said target is a non-axially acting transformation element which transmits the kinetic energy of said thrust element onto a proximal end of said thrust transmitter.

2. A treatment system according to claim 1, including at least two acceleration paths.

3. A treatment system according to claim 1, wherein said thrust element has a cylindrical shape with a rounded front surface and lateral contractual rings.

4. A treatment system according to claim 1, wherein the fact that said thrust element is a ball.

5. A treatment system according to claim 1, wherein pneumatic system drives said thrust element.

6. A treatment system according to claim 1, wherein said thrust element is driven by at least one manually tensioned spring.

7. A treatment system according to claim 1, wherein an electromagnetic system drives said thrust element.

8. A treatment system according to claim 1, wherein said thrust transmitter is a hollow probe.

9. A treatment system according to claim 8, wherein said hollow probe runs at its proximal end into a continuing pipe, said thrust element having an axial borehole which slides over said hollow probe.

10. A treatment system according to claim 8, wherein a channel in said hollow probe serves as a suction or rinsing channel.

11. A treatment system according to claim 8, wherein a channel in said hollow probe receives the probe of a further lithotripsy system.

12. A treatment system according to claim 8, wherein an acoustical sensor which permits stone/soft tissue detection is provided at a proximal end of said hollow probe.

13. An intracorporal treatment system for crushing concretions, such as stones in the urinary tract, calcium deposits in the blood vessels or bone cement, having
    a thrust unit with a thrust element which accelerates a cocking lever in an acceleration path in such a manner that said cocking lever which is a non-axially acting transformation element impinges upon a target, and
    a thrust transmitter designed as a probe which can be inserted into a human body and which is moved by the target in order to transmit the thrust to the treatment site.

14. A treatment system according to claim 13, having multiple thrust elements including a second cocking lever.

15. A treatment system according to claim 14, wherein the kinetic energy of said multiple thrust elements is simultaneously coupled into said thrust transmitter.

16. A treatment system according to claim 14, wherein said kinetic energy of multiple thrust elements is coupled into said thrust transmitter in short succession in comparison to a pulse width of a thrust.

17. An intracorporal treatment system for crushing concretions at a treatment site, such as stones in the urinary tract, calcium deposits in the blood vessels or bone cement, having
    a thrust unit which accelerates a thrust element in an acceleration path in such a manner that it impinges upon a target, and
    a thrust transmitter designed as a probe which can be inserted into a human body and which is moved by the target in order to transmit the thrust to the treatment site, characterized by the fact that said target is a non-axially acting transformation element which transmits the kinetic energy of said thrust element onto proximal end of said thrust transmitter.

* * * * *